US011422346B2

United States Patent
Iida et al.

(10) Patent No.: US 11,422,346 B2
(45) Date of Patent: Aug. 23, 2022

(54) MEDICAL OBSERVATION DEVICE, IMAGE MOVEMENT CORRECTING METHOD, AND MEDICAL OBSERVATION SYSTEM

(71) Applicant: Sony Olympus Medical Solutions Inc., Tokyo (JP)

(72) Inventors: Kenichi Iida, Saitama (JP); Kenji Hirose, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 188 days.

(21) Appl. No.: 16/087,417

(22) PCT Filed: Mar. 10, 2017

(86) PCT No.: PCT/JP2017/009651
§ 371 (c)(1),
(2) Date: Sep. 21, 2018

(87) PCT Pub. No.: WO2017/169650
PCT Pub. Date: Oct. 5, 2017

(65) Prior Publication Data
US 2019/0107699 A1    Apr. 11, 2019

(30) Foreign Application Priority Data
Mar. 31, 2016    (JP) .............................. JP2016-070022

(51) Int. Cl.
*G02B 21/00*    (2006.01)
*H04N 7/18*    (2006.01)
(Continued)

(52) U.S. Cl.
CPC ...... *G02B 21/0012* (2013.01); *A61B 1/00006* (2013.01); *A61B 1/00009* (2013.01);
(Continued)

(58) Field of Classification Search
CPC ................ G02B 21/00; G02B 21/0012; A61B 1/00006; A61B 1/00009; A61B 1/00039; A61B 1/04; H04N 7/18; H04N 7/183
(Continued)

(56) References Cited

U.S. PATENT DOCUMENTS

| | | | | |
|---|---|---|---|---|
| 2003/0069471 A1* | 4/2003 | Nakanishi | ............ | A61B 1/0005 600/101 |
| 2008/0159653 A1* | 7/2008 | Dunki-Jacobs | .......... | A61B 1/04 382/293 |

(Continued)

FOREIGN PATENT DOCUMENTS

| | | |
|---|---|---|
| CN | 102905641 A | 1/2013 |
| CN | 104837432 A | 8/2015 |

(Continued)

OTHER PUBLICATIONS

International Search Report dated May 16, 2017 in PCT/JP2017/009651 filed Mar. 10, 2017.
(Continued)

*Primary Examiner* — Thong Q Nguyen
(74) *Attorney, Agent, or Firm* — Xsensus LLP

(57) ABSTRACT

A medical observation device includes: an imaging section that acquires imaged video data obtained by photographing an observation target; a supporting section that supports the imaging section; a discriminating section that discriminates existence or nonexistence of an input of a visual field moving instruction to an image to be displayed on a display on a basis of the imaged video data and existence or nonexistence of an occurrence of an image movement to an image to be displayed on the display on a basis of the imaged video data; and a correcting section that creates display video data being video data to be displayed on the display on a basis of the imaged video data by correcting the image movement in a case where the discriminating section has (Continued)

discriminated that there does not exist an input of the visual field moving instruction and the image movement is occurring.

17 Claims, 7 Drawing Sheets

(51) Int. Cl.
  *A61B 1/00* (2006.01)
  *A61B 90/20* (2016.01)
  *G02B 27/64* (2006.01)
  *A61B 1/04* (2006.01)
  *A61B 90/25* (2016.01)
  *A61B 90/00* (2016.01)
  *A61B 34/20* (2016.01)

(52) U.S. Cl.
  CPC ............ *A61B 1/00039* (2013.01); *A61B 1/04* (2013.01); *A61B 90/20* (2016.02); *G02B 21/00* (2013.01); *G02B 27/646* (2013.01); *H04N 7/18* (2013.01); *H04N 7/183* (2013.01); *A61B 1/0016* (2013.01); *A61B 1/00149* (2013.01); *A61B 1/00188* (2013.01); *A61B 90/25* (2016.02); *A61B 90/36* (2016.02); *A61B 2034/2048* (2016.02); *A61B 2090/371* (2016.02)

(58) Field of Classification Search
  USPC .................................. 359/368–390, 554–557
  See application file for complete search history.

(56) References Cited

U.S. PATENT DOCUMENTS

| | | | |
|---|---|---|---|
| 2008/0278781 A1 | 11/2008 | Sander | |
| 2009/0020666 A1 | 1/2009 | Brenner | |
| 2012/0262559 A1* | 10/2012 | On | H04N 5/23267 348/65 |
| 2013/0165753 A1* | 6/2013 | Takahashi | A61B 1/00186 600/109 |
| 2015/0080907 A1* | 3/2015 | Herrell | A61B 1/00133 606/130 |
| 2015/0272564 A1* | 10/2015 | Piskun | A61B 1/00087 600/114 |
| 2017/0027416 A1 | 2/2017 | Hayashi | |
| 2017/0135563 A1* | 5/2017 | Uemori | H04N 5/3532 |

FOREIGN PATENT DOCUMENTS

| | | |
|---|---|---|
| CN | 104869937 A | 8/2015 |
| JP | H05-049599 A | 3/1993 |
| JP | 2005-6960 A | 1/2005 |
| JP | 2005-198700 A | 7/2005 |
| JP | 2012-239644 A | 12/2012 |
| WO | WO 2015/046081 A1 | 4/2015 |
| WO | WO 2015/115073 A1 | 8/2015 |

OTHER PUBLICATIONS

Extended European Search Report dated Mar. 4, 2019 in European Patent Application No. 17774194.9, 8 pages.
Office Action dated Oct. 20, 2020, in Japanese Patent Application No. 2018-508927, 8 pages.

* cited by examiner

MEDICAL OBSERVATION DEVICE, IMAGE MOVEMENT CORRECTING METHOD, AND MEDICAL OBSERVATION SYSTEM

TECHNICAL FIELD

The present disclosure relates to a medical observation device, an image movement correcting method, and a medical observation system.

BACKGROUND ART

For example, in surgery (so-called microsurgery) in which microscopic regions such as neurosurgery become a target, observation devices are used for observing a surgical site by enlarging it. An observation device includes a microscope section supported by an arm section (supporting section) (for example, Patent Literature 1).

Here, the microscope section of the observation device described in Patent Literature 1 is an optical type, and a surgeon observes a surgical site by looking into the microscope section directly from an eyepiece section disposed in the microscope section. Hereinafter, an observation device equipped with a microscope section of an optical type is also referred to as an optical type observation device. Until now, as an observation device, such an optical type observation device has been the mainstream.

On the other hand, in recent years, due to the facts that the image processing technology has progressed, and that making an imaged image to high pixels has been realized, in observation devices, those that are equipped with an image sensor and are equipped with an electronic imaging type microscope section capable of photographing a surgical site electronically, have been developed (for example, Patent Literature 2). In the observation device equipped with the microscope section of the electronic imaging type (hereinafter, also referred to as an observation device of an electronic imaging type), an image of a surgical site photographed by the microscope section is displayed on a display device installed in an operating room, and a surgeon performs surgery while observing the surgical site by enlarging it via the display device.

CITATION LIST

Patent Literature

Patent Literature 1: JP 2005-6960A
Patent Literature 2: WO 2015/046081

DISCLOSURE OF INVENTION

Technical Problem

In the observation device of an electronic imaging type, as described in the above, since a surgeon performs surgery while observing the display device, its microscope section and arm section are required not to interrupt a visual field of the surgeon who observes the display device, as much as possible. Therefore, to the microscope section and supporting section of the observation device of the electronic imaging type, a request for miniaturization is large.

However, if the supporting section is made small in size and thin in diameter, its rigidity becomes small. Accordingly, the supporting section becomes to deform elastically easily. Here, in the observation device, when a user moves a microscope section to a position where a desired visual field is acquired, a mode in which the user grips the microscope section directly by hand and moves the microscope section, is supposed. At this time, in the case where the rigidity of the supporting section is comparatively small, along with the moving operation for the microscope section by the user, the supporting section may elastically deform comparatively greatly. Therefore, when the user moves the microscope section to a desired position and releases a hand, the supporting section may elastically restore so that the microscope section may move unintentionally, and a phenomenon in which the visual field moves, may occur. In the following description, such a phenomenon in which a visual field in an image on a display screen moves due to the movement of the microscope section caused by the elastic restoration of the supporting section and an image on the display screen shifts from a desired image, is made to be referred to as an image shift.

If an image shift arises, it is necessary to perform fine adjustment for the position of the microscope section. For this reason, the image shift increases user's mental and physical burden, and in addition, has become a cause to disturb the smooth execution of surgery and to increase a surgery time.

On the other hand, owing to the progress of the image processing technology in recent years, in the observation device of an electronic imaging type, it is becoming possible to photograph an image with higher resolution such as 4K, 8K, or the like. If photographing with high resolution becomes possible, even in the case of having used a display device with a larger screen of, for example, 50 inches or more, it becomes possible to display a surgical site clearly. Moreover, if photographing with high resolution becomes possible, even in the case of displaying an image by enlarging it with an electronic zoom function, it is possible to acquire a clear image. For example, in the case of enlarging an image with an electronic zoom function to two times if it is 4K, or four times if it is 8K, it is possible to secure Full HD image quality. Therefore, since an optical zoom function is not required to have an enlarging performance up to that, an optical system mounted in a microscope section can be simplified more. In this way, in the electronic imaging type observation device capable of performing photographing with high resolution, since the microscope section can be miniaturized more, it can contribute to the securing of the visual field of a surgeon.

However, in the case of displaying an image on a large screen, an apparent size of a shift amount in the above-described image shift (a size of a shift amount on a screen) becomes larger as compared with the case of having used a small size display device. Moreover, also in the case of enlarging an image more with an electronic zoom function in addition to the optical zoom function, a shift amount in the above image shift becomes larger more. Thus, in the electronic imaging type observation device, in the case of performing photographing especially with high resolution, there is a fear that a slight movement of a microscope section becomes a large image shift.

On the other hand, in the observation device, for example, due to the walking or the like of a medical staff moving in the inside of an operating room, the microscope section may vibrate. Since such vibration causes unintended shake of an image (image shake) in observation by enlarging, work cannot be performed until this shake stops. Accordingly, it has made the mental burden of a surgeon increase, and, has become a cause of lowering the efficiency of surgery.

In view of the above-described situation, in the medical observation devices, it is considered that if occurrence of an image shift and/or image shake (hereinafter, collectively referred to as an unintended image movement) can be depressed, medical practices, such as surgery and inspection, can be performed more smoothly, and it becomes possible to enhance safety more. Then, the present disclosure proposes a novel and improved medical observation device capable of enhancing the safety of medical practices, such as surgery and inspection, an image movement correcting method, and a medical observation system.

Summary

According to the present disclosure, there is provided a medical observation device, including: an imaging section that acquires imaged video data being video data obtained by photographing an observation target; a supporting section that supports the imaging section; a discriminating section that discriminates existence or nonexistence of an input of a visual field moving instruction to an image to be displayed on a display device on a basis of the imaged video data and existence or nonexistence of an occurrence of an image movement to an image to be displayed on the display device on a basis of the imaged video data; and a correcting section that creates display video data being video data to be displayed on the display device on a basis of the imaged video data by correcting the image movement in a case where the discriminating section has discriminated that there does not exist an input of the visual field moving instruction and the image movement is occurring.

In addition, according to the present disclosure, there is provided an image movement correcting method, including: capturing imaged video data being video data obtained by photographing an observation target; discriminating, by a processor, existence or nonexistence of an input of a visual field moving instruction to an image to be displayed on a display device on a basis of the imaged video data and existence or nonexistence of an occurrence of an image movement to an image to be displayed on the display device on a basis of the imaged video data; and a correcting section that creates display video data being video data to be displayed on the display device on a basis of the imaged video data by correcting the image movement in a case where it has been discriminated that there does not exist an input of the visual field moving instruction and the image movement is occurring.

In addition, according to the present disclosure, there is provided a medical observation system, including: a medical observation device that photographs an observation target; and a display device that displays an image of the observation target photographed by the medical observation device. The medical observation device includes an imaging section that acquires imaged video data being video data obtained by photographing an observation target, a supporting section that supports the imaging section, a discriminating section that discriminates existence or nonexistence of an input of a visual field moving instruction to an image to be displayed on the display device on a basis of the imaged video data and existence or nonexistence of an occurrence of an image movement to an image to be displayed on the display device on a basis of the imaged video data, and a correcting section that creates display video data being video data to be displayed on the display device on a basis of the imaged video data by correcting the image movement in a case where the discriminating section has discriminated that there does not exist an input of the visual field moving instruction and the image movement is occurring.

According to the present disclosure, in a medical observation device including an imaging section supported by a supporting section, in the case where there does not exist an input of a visual field moving instruction (i.e., a movement of a visual field intended by a user is not performed) and an image movement is occurring, a process of correcting the image movement is executed. Therefore, for example, even if the supporting section is comparatively thin and its rigidity is small, it becomes possible to acquire a more stable image in which an image movement unintended by a user has been suppressed. Accordingly, it becomes possible to perform surgery more smoothly and more safely.

Advantageous Effects of Invention

As described in the above, according to the present disclosure, it becomes possible to enhance the safety of medical practices, such as surgery and inspection, more. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
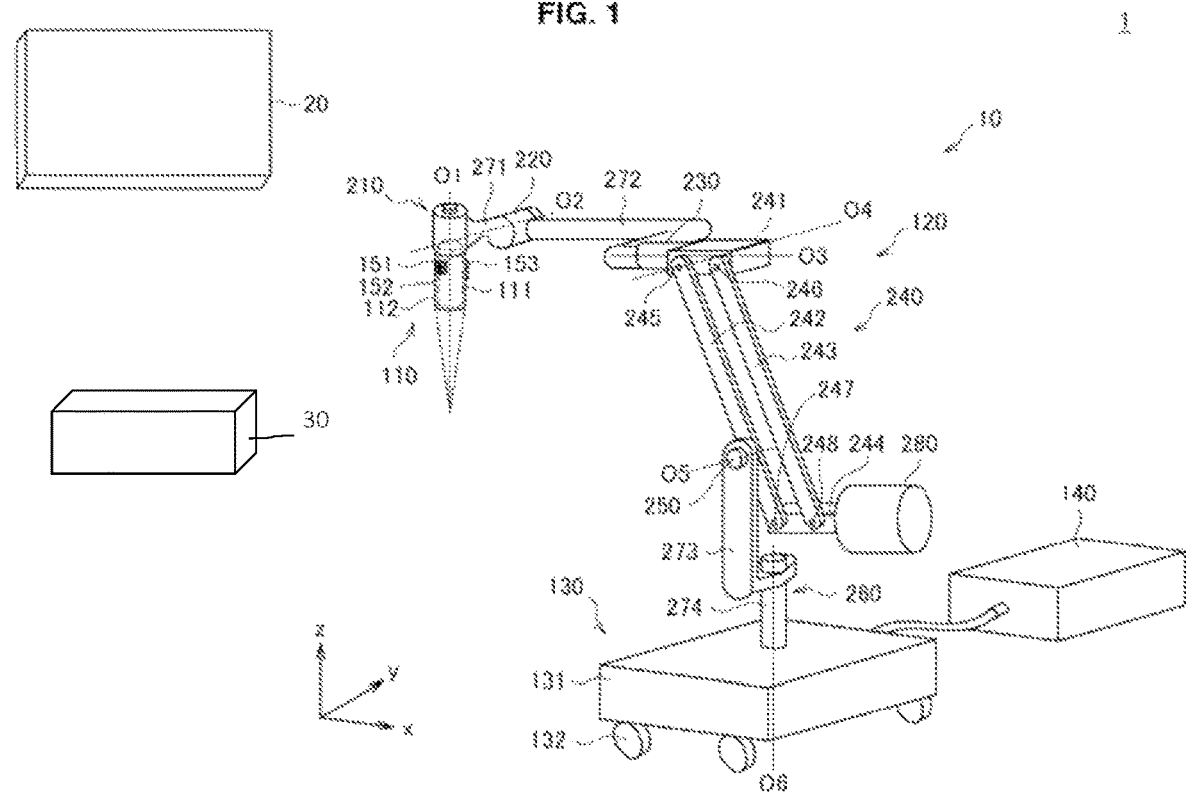
FIG. 1 is an illustration showing a constitution of an observation system according to the first embodiment.

Hereinafter, (a) preferred embodiment(s) of the present disclosure will be described in detail with reference to the appended drawings. In this specification and the appended drawings, structural elements that have substantially the same function and constitution are denoted with the same reference numerals, and repeated explanation of these structural elements is omitted.

It should be noted that description will be given in the following order.

1. First embodiment
1-1. Constitution of observation system
1-2. Functional constitution of image movement correcting system
1-3. Image movement correcting method
2. Second embodiment
2-1. Functional constitution of image movement correcting system
2-2. Image movement correcting method
3. Supplement In this connection, in the description in the below, a user who uses a later-mentioned observation system and image movement correcting system and a user who operates a later-mentioned observation device are described as a surgeon for the sake of convenience. However, this description does not limit the user who uses the observation system and the image movement correcting system and the user who operates the observation device, and a main actor who uses these systems and a main actor who operates the observation device may be other medical staffs, such as an assistant and a nurse.

1. First Embodiment (1-1. Constitution of Observation System)

The constitution of an observation system according to a first embodiment of the present disclosure, and an observation device that forms the observation system, will be described with reference to FIG. 1. FIG. 1 is a view illustrating a configuration of the observation system according to the first embodiment.

Referring to FIG. 1, the observation system 1 according to the first embodiment includes an observation device 10 that supports a microscope section 110 and photographs an image of a surgical site of a patient with the microscope section 110, and a display device 20 that displays the image of the surgical site photographed by the observation device 10. The observation system 1 is a medical observation system for observing an observation target portion (surgical target portion (surgical site) or inspection target portion) being a part of a patient's body at the time of performing medical practices, such as surgery and inspection. At the time of surgery or at the time of inspection, a surgeon observes a target portion while referring an image photographed by the observation device 10 and displayed on the display device 20, and, performs various kinds of treatments for the target portion if needed. Hereinafter, description is given for a case of performing surgery by using the observation system 1, and its observation target portion is also referred to as a surgical site.

(Display Device)

Under the control of the control device 140 described later, the display device 20 displays the image of the patient's surgical site photographed by the observation device 10. The display device 20 is installed in a location visible to the surgeon in an operating room, such as on a wall of the operating room, for example. The type of the display device 20 is not particularly limited, and any of various publicly known types of display devices may be used as the display device 20, such as a cathode ray tube (CRT) display device, a liquid crystal display device, a plasma display device, or an electroluminescence (EL) display device. Additionally, the display device 20 is not necessarily required to be installed inside the operating room, and may also be mounted onboard a device used by being worn on the surgeon's body, such as a head-mounted display (HMD) or an eyeglasses-type wearable device.

Note that, as will be described later, in a case in which an imaging section 111 of the microscope section 110 of the observation device 10 is configured as a stereo camera, or such that high-resolution imaging is possible, a display device 20 capable of 3D display or capable of displaying an image with high resolution may be used accordingly.

(Observation Device)

The observation device 10 is equipped with a microscope section 110 for performing enlarged observation of the patient's surgical site, a supporting section 120 (arm section 120) that holds the microscope section 110, a base section 130 to which one end of the supporting section 120 is connected and which supports the microscope section 110 and the supporting section 120, and a control device 140 that controls the operation of the observation device 10 and the observation system 1.

(Base Section)

The base section 130 supports the microscope section 110 and the supporting section 120. The base section 130 includes a platform 131 having a planar shape, and multiple casters 132 provided on the bottom face of the platform 131. One end of the supporting section 120 is connected to the top face of the platform 131, while the microscope section 110 is connected to the other end of the supporting section 120 extending from the platform 131 (the tip end). Also, the observation device 10 is in contact with the floor through the casters 132, and is configured to be movable across the floor by the casters 132.

Note that in the following description, the direction perpendicular to the floor on which the observation device 10 is installed is defined to be the z-axis direction. The z-axis direction is also called the up-and-down direction or the vertical direction. Additionally, the two mutually orthogonal directions to the z-axis direction are defined to be the x-axis direction and the y-axis direction. The direction parallel to the x-y plane is also called the horizontal direction.

(Microscope Section)

The microscope section 110 is made up of a microscope body for performing enlarged observation of the patient's surgical site. In the illustrated example, the optical axis direction of the microscope section 110 is approximately aligned with the z-axis direction. The microscope section 110 has a configuration corresponding to a microscope section of the electronic imaging type, and is made up of a barrel section 112 having an approximately cylindrical shape, and an imaging section 111 provided inside the barrel section 112. The imaging section 111 is made up of an optical system that includes a lens such as an objective lens and a focus lens, and an optical sensor such as a mirror, and an image sensor that photographs an image of the surgical site that is to be observed with light passing through the optical system.

The aperture on the bottom end of the barrel section 112 is provided with a cover glass for protecting the imaging section 111. A light source is also provided inside the barrel section 112, and during image photograph, the subject is irradiated with illuminating light radiating from the light source through the cover glass. Of this illuminating light, the light reflecting back from the subject (observation light) is incident on the imaging section 111 via the cover glass, and as a result, a signal related to the image of the subject (video signal) is acquired by the imaging section 111.

For the imaging section 111, it is sufficient to apply a configuration used in any of various publicly known types of electronic imaging microscope sections, and for this reason a detailed description thereof will be reduced or omitted herein. For example, any of various publicly known types of image sensors may be applied as the image sensor of the imaging section 111, such as a charge-coupled device (CCD) sensor or a complementary metal-oxide-semiconductor (CMOS) sensor. Additionally, the imaging section 111 may be capable of 3D display to also be configured as a stereo camera equipped with a pair of image sensors. Also, any of various publicly known types of configurations may be applied to the optical system of the imaging section 111. Furthermore, any of various types of functions typically provided in electronic imaging microscope sections, such as an autofocus (AF) function and an optical zoom function, may be provided onboard the imaging section 111.

In this connection, in the first embodiment, it is preferable that the imaging section 111 is constituted so as to be able to perform photographing with high resolution, such as 4K, 8K or the like. By making the imaging section 111 to be constituted so as to be able to perform photographing with high resolution, since it becomes possible to display an image on the display device 20 with a large screen of, for example, 50 inches or more while securing predetermined resolution, the visibility of a surgeon improves. Moreover, by making the imaging section 111 to be constituted so as to be able to perform photographing with high resolution, even if an image is displayed by being enlarged appropriately with an electronic zoom function, it becomes possible to secure predetermined resolution. For example, even in the case where an image is enlarged with the electronic zoom function by two times if it is 4K, by four times if it is 8K, or by eight times if it is 16K, it is possible to secure Full HD image quality. With this, the microscope section 110 is not requested to have an optical zoom function up to that, and it becomes possible to make the optical system of the microscope section 110 simple. Accordingly, it becomes possible to constitute the microscope section 110 to be smaller in size. As mentioned later, in order to secure the visual field of a surgeon, although it is preferable that the microscope section 110 is smaller in size, by constituting the imaging section 111 so as to be able to perform photographing with high resolution, it is possible to attain the effect capable of making such a microscope section 110 to be further smaller in size. In this connection, in concrete terms, in the first embodiment, in image processing by a later-mentioned control device 140, the magnification of the electronic zoom function can be adjusted to any of 1 time (×1), 1.5 times (×1.5), two times (×2), four times (×4), and eight times (×8). Correspondingly to this, for example, even if the magnification in the electronic zoom function is two times or more, the imaging section 111 may be constituted such that it is possible to perform photographing with the resolution capable of maintaining predetermined resolution (for example, Full HD image quality).

Video signals acquired by the microscope section 110, i.e., video data, are transmitted to the control device 140. In the control device 140, the video data are subjected to various kinds of image processing, such as a gamma correcting process, a white balance adjusting process, an enlarging process according to an electronic zoom function (for example, the magnification is 1 time (×1), 1.5 times (×1.5), two times (×2), four times (×4), or eight times (×8)), and an inter-pixel correcting process. In the image processing, in order to display an image on the display device 20, various kinds of generally-performed image processing may be performed. Moreover, various kinds of setting, such as white balance in the image processing, the magnification of an electronic zoom, and the like, may be set appropriately by a surgeon. However, as mentioned later, in the first embodiment, in the case where occurrence of an unintended image movement has been detected and an image movement has been detected, the control device 140 performs the above-described image processing so as to correct the image movement. In this connection, the details of this image movement correcting process are described again in the below (1-2. Functional Constitution of Image Movement Correcting System).

The video data that has undergone the above-described image processing is transmitted to the display device 20 provided in the operating room, and a video of the surgical site is appropriately enlarged at the desired magnification by the optical zoom function and/or the electronic zoom function, for example, and displayed on the display device 20. Note that communication between the control device 140 and the display device 20 may be realized by any of various publicly known wired or wireless methods.

In this connection, the above-described image processing is not necessarily performed by the control device 140. For example, a processing circuit for performing the above-mentioned image processing may be disposed in the microscope section 110. In this case, video data after having been subjected to image processing appropriately in the processing circuit mounted on the microscope section 110 may be transmitted from the microscope section 110 to the display device 20. Also, in this case, the communication between the microscope section 110 and the display device 20 may be realized by any of various publicly known wired or wireless methods.

The microscope section 110 is provided with various types of switches for controlling the operation of the microscope section 110. For example, the microscope section 110 is provided with a zoom switch 151 (zoom SW 151) and a focus switch 152 (focus SW 152) for adjusting the image photograph parameters of the microscope section 110, as well as an operation mode changing switch 153 (operation mode changing SW 153) for toggling the operating mode of the supporting section 120.

The surgeon, by operating the zoom SW 151 and the focus SW 152, is able to adjust the magnification and the focal length of the microscope section 110, respectively. Also, by operating the operation mode changing SW 153, the surgeon is able to toggle the operating mode of the supporting section 120 between a locked mode and a free mode.

Herein, the locked mode is an operating mode in which the position and the attitude of the microscope section 110 are locked by using a brake to restrain rotation about each rotation axis provided in the supporting section 120. The free mode is an operating mode in which the brake is released, thereby allowing free rotation about each rotation axis provided in the supporting section 120. For example in the free mode, it is possible to adjust the position and the attitude of the microscope section 110 with direct operations by the surgeon. Herein, direct operations mean operations in which the surgeon grips the microscope section 110 with his or her hand, for example, and directly moves the microscope section 110. For example, the operating mode of the supporting section 120 becomes the free mode while the surgeon is pressing the operation mode changing SW 153, and the operating mode of the supporting section 120 becomes the locked mode while the surgeon releases his or her hand from the operation mode changing SW 153.

Note that these switches are not necessarily required to be provided on the microscope section 110. In the first embodiment, it is sufficient for the observation device 10 to be provided with a mechanism for accepting operating input having functions similar to these switches, and the specific configuration of such a mechanism is not limited. For example, these switches may also be provided on another section of the observation device 10. As another example, an input device such as a remote control, a foot switch or the like may be used, and commands corresponding to these switches may be input into the observation device 10 remotely.

Also, although the barrel section 112 of the microscope section 110 is illustrated as a simple cylindrically-shaped member in FIG. 1 for the sake of simplicity, the barrel section 112 may also be provided with a grip section gripped by the surgeon. Such a grip section may be realized by having a constitution such as a handle to be gripped by the surgeon be formed around the outer circumference of the barrel section 112. Alternatively, such a grip section may be realized by having the shape of the barrel section 112 be formed into a shape that is gripped easily by the surgeon. For example, as described above, when in the free mode, operations of moving the microscope section 110 with the surgeon gripping the barrel section 112 directly in hand may be anticipated. At this point, since the surgeon performs an operation of moving the microscope section 110 while pressing the operation mode changing SW 153, the shape of the barrel section 112 and the placement of the operation mode changing SW 153 may be determined appropriately with consideration for operability by the surgeon while in the free mode. In addition, the placement of the zoom SW 151 and the focus SW 152 may be determined appropriately with similar consideration for operability by the surgeon.

(Control Device)

The control device 140 may be a processor, such as a central processing section (CPU) or a digital signal processor (DSP), for example, or a control board on which these processors and memory sensors such as memory are mounted together with components. Various functions of the control device 140 are realized by the processor that forms the control device 140 executing calculation processes in accordance with a predetermined program.

For example, the control device 140 includes a function of toggling the operating mode of the supporting section 120 discussed earlier by controlling the driving of the brake provided in each rotational axis section of the supporting section 120 in response to operating input performed by the surgeon via the above operation mode changing SW 153. As another example, the control device 140 includes a function of appropriately driving the optical system in the imaging section 111 of the microscope section 110 to adjust the magnification and the focal length of the microscope section 110 in response to operating input performed by the surgeon via the above zoom SW 151 and focus SW 152. Also, the control device 140 has a function of performing various kinds of image processing on the video data acquired by the microscope section 110, and displaying an image based on the processed video data on the display device 20. At this time, in the first embodiment, the image movement correcting process is performed by the control device 140 if needed, and an image in which an unintended image movement has been suppressed is displayed on the display device 20.

Note that in the illustrated example, the control device 140 is provided as a separate configuration from the microscope section 110, the supporting section 120, and the base section 130, and is connected to the base section 130 by a cable. However, the first embodiment is not limited to such an example. For example, a processor, a control board, or the like that realizes functions similar to the control device 140 may also be disposed inside the base section 130. Additionally, by incorporating a processor, a control board, or the like that realizes functions similar to the control device 140 into the microscope section 110 internally, the control device 140 and the microscope section 110 may be configured in an integrated manner. Alternatively, functions similar to the functions of the control device 140 may be realized by a processor or a control board or the like being arranged in each rotational axis section that forms the supporting section 120, and having these plurality of processors or control boards or the like work together.

(Supporting Section)

A supporting section 120 moves the microscope section 110 three dimensionally, and, supports the microscope section 110 at the position and attitude fixedly after the moving. In the first embodiment, the supporting section 120 is constituted as a balance arm having six degrees of freedom. However, the first embodiment should not be limited to this example, and, the supporting section 120 may be constituted so as to be able to move the microscope section 110 appropriately in accordance with an intended use, and, may be constituted so as to have other different number of degrees of freedom.

The supporting section 120 is provided with six rotational axes (the first axis $O_1$, the second axis $O_2$, the third axis $O_2$, the fourth axis $O_4$, the fifth axis $O_5$ and the sixth axis $O_6$) corresponding to the six degrees of freedom. Hereinafter, for convenience for description, it is assumed that the members that constitute respective rotational axes are collectively referred to as a rotational axis section. For example, the rotational axis section may include a bearing, a shaft inserted rotatably through the bearing, a brake to regulate the rotation on the rotational axis, and so on. A later-mentioned parallelogram link mechanism 240 can be deemed also as one of the rotational axis section.

The supporting section 120 includes a first rotational axis section 210, a second rotational axis section 220, a third rotational axis section 230, a fourth rotational axis section 240, a fifth rotational axis section 250, and a sixth rotational axis section 260 corresponding to the respective rotation axes; a first arm section 271, a second arm section 272, a third arm section 273, and a fourth arm section 274 that are connected rotatably to each other by these first rotational axis section 210 to sixth rotational axis section 260; and a counter weight 280 for taking balance of moment of the microscope section 110 and the supporting section 120 as a whole. In this connection, the fourth rotational axis section 240 corresponds to the parallelogram link mechanism 240.

Note that in the description below, when describing the constitution of the supporting section 120, the side on which the microscope section 110 is provided will also be referred to as the tip end side or the tip end portion or the like, and the side near the base section 130 will also be referred to as the base end side or the base end portion or the like.

The first rotational axis section 210 has a generally cylindrical shape, and is connected to the base end portion of the barrel section 112 of the microscope section 110 such that the central axis of the first joint section 210 is substantially coincident with the central axis of the barrel section 112 of the microscope section 110. The first rotational axis section 210 rotatably supports the microscope section 110, with the direction substantially coincident with the optical axis of the microscope section 110 as the rotational axis direction (the direction of the first axis $O_1$). In the example illustrated in FIG. 1, the first axis $O_1$ is provided as a rotational axis that is substantially parallel to a z-axis. The orientation of the image photographed by the microscope section 110 is adjusted by rotating the microscope section 110 about the first axis $O_1$ by the first rotational axis section 210.

Note that in the illustrated example, a portion of the imaging section 111 of the microscope section 110 is housed inside a cylindrical case that forms the first rotational axis section 210. That is, the microscope section 110 and the first rotational axis section 210 are configured as an integrated member. However, the present embodiment is not limited to this example. The first rotational axis section 210 and the microscope section 110 may also be configured as separate members.

A tip end of the first arm section 271 that extends in a direction substantially perpendicular to the first axis $O_1$ is connected to the first rotational axis section 210. Also, the second rotational axis section 220 that rotatably supports the first arm section 271, with a direction substantially parallel to the direction in which the first arm section 271 extends as the rotational axis direction (the direction of the second axis $O_2$), is provided on a base end of the first arm section 271. The second axis $O_2$ is a rotational axis that is substantially perpendicular to the first axis $O_1$, and is provided as a rotational axis that is substantially parallel to the y-axis in the example illustrated in FIG. 1. The position in the x-axis direction of the microscope section 110 is adjusted by rotating the microscope section 110 and the first arm section 271, with the second axis $O_2$ as the rotational axis, by the second rotational axis section 220.

To the second rotational axis section 220, connected is the tip of the second arm section 272 that extends in a direction approximately vertical mutually to the first axis $O_1$ and the second axis $O_2$. Moreover, a base side of the second arm section 272 is bent in an almost L form, and on a position corresponding to a folded short side, disposed is the third rotational axis section 230 that makes a direction almost parallel to the stretching direction of a portion corresponding to the long side of the second arm section 272 to the rotational axis direction (the third axis $O_3$ direction) and supports the second arm section 272 rotatably. The third axis $O_3$ is a rotational axis almost vertical to the first axis $O_1$ and the second axis $O_2$, and, in an example shown in FIG. 1, is disposed as a rotational axis almost parallel to the x axis. With the third rotational axis section 230, on the third axis $O_3$ serving as a rotational axis, the microscope section 110, the first arm section 271, and the second arm section 272 are made to rotate, whereby the position, in the y axis direction, of the microscope section 110 will be adjusted.

In this way, the supporting section 120 is configured such that the attitude of the microscope section 110 is controlled by controlling the rotation about both the second axis $O_2$ and the third axis $O_3$. That is, the second rotational axis section 220 and the third rotational axis section 230 can be rotational axis sections that define the attitude of the microscope section 110.

To the base end side of the third rotational axis section 230, the tip of the upper side of the parallelogram link mechanism 240 is connected. The parallelogram link mechanism 240 includes four arms (arms 241, 242, 243, and 244) arranged in the form of a parallelogram, and four joint sections (joint sections 245, 246, 247, and 248) disposed at the respective positions corresponding to the almost vertexes of the parallelogram.

The tip end of the arm 241 that extends in a direction substantially parallel to the third axis $O_3$ is connected to the third rotational axis section 230. The joint section 245 is provided near the tip end of the arm 241, and the joint section 246 is provided near the base end of the arm 241. The tip ends of the arms 242 and 243 are connected to the joint sections 245 and 246, respectively, in a manner that enables the tip ends of the arms 242 and 243 to rotate about rotational axes (the fourth axis $O_4$) that are substantially perpendicular to the direction in which the arm 241 extends, and substantially parallel to each other. Moreover, the joint sections 247 and 248 are provided on base ends of the arms 242 and 243, respectively. A tip end and a base end of the arm 244 are connected to these joint sections 247 and 248, respectively, in a manner able to rotate about the fourth axis $O_4$ and substantially parallel to the arm 241.

In this way, the four joint sections that form the parallelogram link mechanism 240 have rotational axes (the fourth axis $O_4$) in substantially the same direction that are substantially parallel to each other, and operate in conjunction with each other about the fourth axis $O_4$. In the example illustrated in FIG. 1, the fourth axis $O_4$ is provided as a rotational axis that is substantially parallel to the y-axis. That is, the parallelogram link mechanism 240 is configured to have a plurality of joint sections that are arranged in different positions from each other, and that rotate in conjunction with each other on rotational axes that are in the same direction, such that the parallelogram link mechanism 240 behaves as a transmission mechanism that transmits operation at one end to the other end. By disposing the parallelogram link mechanism 240, the movement of the constitutions (i.e., the microscope section 110, the first rotational axis section 210, the second rotational axis section 220, the third rotational axis section 230, the first arm section 271, and the second arm section 272) on the tip end side than the parallelogram link mechanism 240, is transmitted to the base end side of the parallelogram link mechanism 240.

The fifth rotational axis section 250 that rotatably supports the parallelogram link mechanism 240, with a direction perpendicular to the direction in which the arm 242 extends as the rotational axis direction (the direction of the fifth axis $O_5$), is provided on a portion a predetermined distance away from the base end of the arm 242. The fifth axis $O_5$ is a rotational axis that is substantially parallel to the fourth axis $O_4$, and is provided as a rotational axis that is substantially parallel to the y-axis in the example illustrated in FIG. 1. To the fifth rotational axis section 250, the tip end of the third arm section 273 being stretched in the z axis direction is connected, and the microscope section 110, the first arm section 271, the second arm section 272, and the parallelogram link mechanism 240 are constituted to be rotatable relative to the third arm section 273 on the fifth axis $O_5$ serving as a rotational axis via the fifth rotational axis section 250.

The third arm section 273 has a form of an almost L shape, and its base end side is bent so as to become almost parallel to a floor. To a surface, almost parallel to the floor, of the third arm section 273, connected is the sixth rotational axis section 260 on which the third arm section 273 is rotatable around a rotational axis (the sixth axis $O_6$) orthogonal to the fifth axis $O_5$. In the example shown in FIG. 1, the sixth axis $O_6$ is disposed as a rotational axis almost parallel to the z axis.

In the example shown in the illustration, the sixth rotational axis section 260 is constituted integrally with the fourth arm section 274 extending in the vertical direction. That is, the tip end of the fourth arm section 274 is connected to the surface, almost parallel to the floor, of the base end of the third arm section 273. Moreover, the base end of the fourth arm section 274 is connected to the upper surface of the platform 131 of the base section 130. With this constitution, the microscope section 110, the first arm section 271, the second arm section 272, the parallelogram link mechanism 240, and the third arm section 273 rotates relative to the base section 130 on the sixth $O_6$ serving as a rotational axis via the sixth rotational axis section 260.

The arm 244 that forms the lower side of the parallelogram link mechanism 240 is formed longer than the arm 241 that forms the upper side of the parallelogram link mechanism 240, and the end of the arm 242 that is positioned diagonally opposite the portion of the parallelogram link mechanism 240 to which the third rotational axis section 230 is connected extends to the outside of the parallelogram link mechanism 240. The counterweight 280 is provided on the extending end of the arm 244. The mass and placement position of the counterweight 280 are adjusted such that the rotation moment generated about the fourth axis $O_4$ and the rotation moment generated about the fifth axis $O_5$ are able to cancel each other out by the mass of the constitutions (i.e., the microscope section 110, the first rotational axis section 210, the second rotational axis section 220, the third rotational axis section 230, the first arm section 271, the second arm section 272, and the parallelogram link mechanism 240) that are arranged to the tip end side of the counterweight 280 itself.

Also, the placement position of the fifth rotational axis section 250 is adjusted such that the center of gravity of each of the constitutions arranged to the tip end side of the fifth rotational axis section 250 is positioned on the fifth axis $O_5$. Moreover, the placement position of the sixth rotational axis section 260 is adjusted such that the center of gravity of each of the constitutions arranged to the tip end side of the sixth rotational axis section 260 is positioned on the sixth axis $O_6$.

By having the mass and placement position of the counterweight 280, the placement position of the fifth rotational axis section 250, and the placement position of the sixth rotational axis section 260 configured in this way, the supporting section 120 can be configured as a balance arm in which the moments of the microscope section 110 and the supporting section 120 are balanced on the whole. By constituting the supporting section 120 as a balance arm, in the case where a surgeon intends to move the microscope section 110 by a direct operation, it becomes possible to move the microscope section 110 with a smaller external force as if it was under weightlessness. Therefore, the operativity of the surgeon can be improved.

The first rotational axis section 210 to the sixth rotational axis section 260 of the supporting section 120 are provided with respective brakes that regulate the rotations on the first rotational axis section 210 to the sixth rotational axis section 260. In this connection, in the parallelogram link mechanism 240, the four joint sections (joint sections 245 to 248) rotate mutually in conjunction with each other. Accordingly, a brake for the parallelogram link mechanism 240 may be disposed for at least any of these four joint sections. The driving of these brakes is controlled by the control device 140. By releasing these brakes all at once under the control from the control device 140, the operational mode of the supporting section 120 shifts to a free mode. Moreover, similarly, under the control from the control device 140, by actuating these brakes all at once, the operational mode of the supporting section 120 shifts to a fixed mode.

In this connection, as the brake disposed in the first rotational axis section 210 to the sixth rotational axis section 260, various kinds of brakes used for a general balance arm may be applied, and its concrete mechanism is not limited. For example, these brakes may be those driven mechanically, or may be electromagnetic brakes driven electrically.

In the above, with reference to FIG. 1, the constitution of the observation system 1 and the observation device 10 according to the first embodiment have been described. In this connection, the observation system 1 and the observation device 10 may be constituted as follows.

For example, an actuator may be mounted on at least one of the respective rotational axis sections of the supporting section 120, and by controlling the driving of the actuator with the control device 140, the control of the position and attitude of the supporting section 120, i.e., the control of the position and attitude of the microscope section 110 may be performed. In this case, for example, in accordance with an operation input performed by a surgeon through various kinds of input devices, such as a remote control terminal, a foot switch, and the like, the supporting section 120 may be operated remotely. Alternatively, the input device may be a pressure sensitive sensor disposed on a partial region of a peripheral surface of the microscope section 110. For example, in the case where a surgeon touches the pressure sensitive sensor, the driving of the above-described actuator may be controlled such that the microscope section 110 moves in the touched direction.

Alternatively, as described in the above, in the case where an actuator is mounted on at least one of the respective rotational axis sections of the supporting section 120, a navigation device 30 that issues an instruction about the movement of the microscope section 110 to the observation device 10 may be disposed in the observation system 1. In this case, upon receipt of an instruction from the navigation device, the control device 140 makes the actuator drive, and the position and attitude of the microscope section 110 may be controlled. In this connection, as the above-described input device or navigation device 30, various kinds of publicly known devices being used when moving a microscope section in a general observation device may be used.

For example, in the observation system 1, although there may arise a desire to move slightly the visual field of an image on a screen of the display device 20, or a desire to move a visual field in parallel in an either direction without changing the top, bottom, left, and right of an image on a screen of the display device 20, there may be a case where, by a direct operation, it is difficult to move the microscope section 110 slightly, or, to shift the microscope section 110 in parallel in either direction within a horizontal plane. In such a case, by controlling the movement of the microscope section 110 with actuators as described in the above, it becomes possible to move the microscope section 110 more correctly to a position where a desired visual field is acquired. In this connection, in the following description, the movement of the microscope section 110 by a direct operation may be referred to as "perform the movement of the microscope section 110 manually", and the movement of the microscope section 110 by the driving of an actuator may be referred to as "perform the movement of the microscope section 110 automatically".

Figure 2:
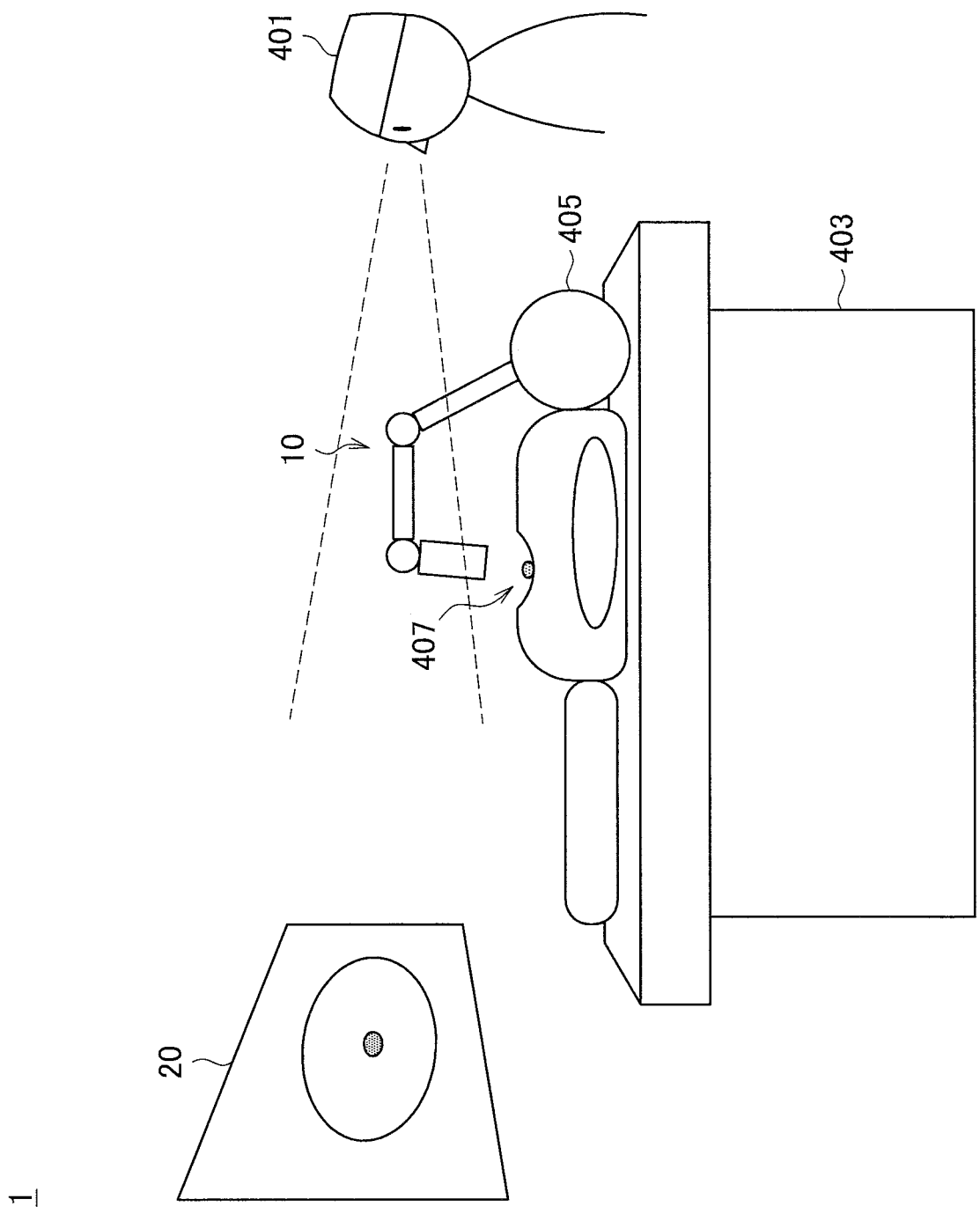
FIG. 2 is an illustration showing a situation of surgery using the observation system shown in FIG. 1.

Here, FIG. 2 is an illustration showing a situation of surgery using the observation system 1 shown in FIG. 1. FIG. 2 shows schematically a situation where a surgeon 401 is performing surgery for a surgical site 407 of a patient 405 on a patient bed 403 using the observation system 1. In this connection, in FIG. 2, for simplicity, the observation device 10 is illustrated by being simplified.

In the observation system 1, an image of the surgical site 407 photographed by the observation device 10 is displayed on the display device 20, and the surgeon 401 performs the surgery while looking at the image on the display device 20. However, in that case, as shown in FIG. 2, between the surgeon 401 and the display device 20, the microscope section 110 and the supporting section 120 of the observation device 10 may be located. Therefore, the microscope section 110 and the supporting section 120 are required to be small in size so as not to interrupt the view field of the surgeon 401 as much as possible.

Therefore, in the first embodiment, the supporting section 120 may be constituted such that the supporting section 120, in particular, its constitution in the vicinity of the microscope section 110 becomes as small as possible in size. With this, the view field of the surgeon 401 who looks at the display device 20 becomes better, and it becomes possible to perform the surgery more smoothly. For example, in order to realize the good view field of the surgeon 401, in the supporting section 120, it is preferable that the diameter of the thinnest portion is 60 mm or less. The diameter of the thinnest portion is more preferably 30 mm or less, still more preferably 20 mm or less, and particularly preferably 10 mm or less. As the diameter of the thinnest portion become smaller, the supporting section 120 is constituted to be smaller in size, whereby it becomes possible to secure the view field of the surgeon 401 further favorably. In this connection, in the supporting section 120, the thinnest (slimmest) portion may be, for example, among the arm sections (the first arm section 271, the second arm section 272, the third arm section 273, and the fourth arm section 274) that constitute the supporting section 120, an arm section disposed comparatively close to the microscope section 110 (for example, close to the second rotational axis section 220 and the third rotational axis section 230 corresponding to a rotational axis (the second axis O₂ and the third axis O) that can regulate the attitude of the microscope section 110). In the constitution example shown in FIG. 1, the second arm section 272 located between the second rotational axis section 220 and the third rotational axis section 230 may correspond to the thinnest portion in the supporting section 120.

However, if the supporting section 120 is made to be smaller in size and thinner in diameter, its rigidity becomes smaller. Here, in the observation device 10, supposed is a mode in which, in a free mode, the surgeon 401 moves the microscope section 110 by a direct operation up to a position where a desired visual field is acquired while looking at an image displayed on a display screen. At this time, in the case where the rigidity of the supporting section 120 is comparatively small, along with the moving operation for the microscope section 110 by the surgeon 401, the supporting section 120 will elastically deform comparatively greatly. Therefore, when the surgeon has moved the microscope section 110 up to a desired position and has released a hand, the supporting section 120 restores elastically, whereby the microscope section 110 moves unintentionally, and image shift may occur.

On the other hand, the observation device 10 may be constituted so as to be able to perform photographing with high resolution as described in the above. With this, it becomes possible to display an image on the display device 20 with a further larger screen while securing predetermined resolution, or to display an image by enlarging it appropriately with an electronic zoom function. However, in the case of performing display on a large screen or enlarged display by electronic zoom in this way, a shift amount in the above-described image shift will become more remarkable.

Thus, it can be said that occurrence of an image shift is a problem peculiar to the observation device of an electronic imaging type like the observation device 10.

On the other hand, in the observation device 10, for example, due to vibration of the floor along with the walking of a medical staff, the microscope section 110 may shake. Alternatively, in the case of having performed the movement of the microscope section 110 automatically as mentioned in the above, the microscope section 110 may shake by inertia at the time of stopping of the microscope section 110. Such unintended vibration of the microscope section 110 becomes a cause of inducing image shake.

In the case where an image shift and/or image shake (i.e., unintended image movement) occurs, there is a fear that it becomes difficult to perform surgery safely smoothly. Therefore, in the observation device of an electronic imaging type, in order to realize safer surgery, it is important to suppress occurrence of unintended image movement.

Then, in the first embodiment, an image movement correcting system for correcting an unintended image movement is incorporated to the above-mentioned observation system 1. With the image movement correcting system, an unintended image movement having occurred during surgery is corrected appropriately, whereby it becomes possible to realize safer surgery.

(1-2. Functional Constitution of Image Movement Correcting System)

Figure 3:
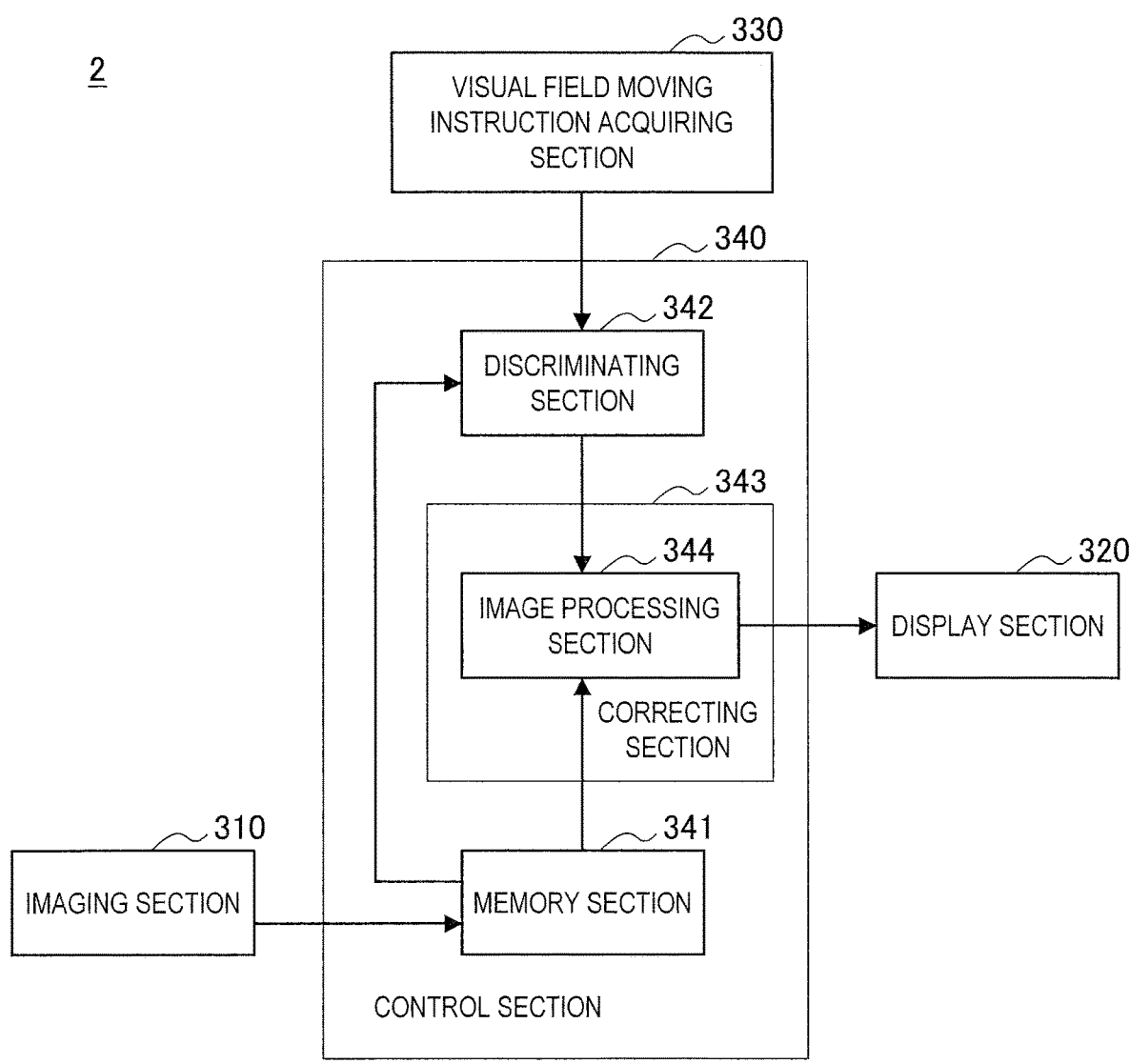
FIG. 3 is a block diagram showing one example of a functional constitution of an image movement correcting system according to the first embodiment.

With reference to FIG. 3, a constitution of the above-described image movement correcting system is described in detail. FIG. 3 is a block diagram showing one example of a functional constitution of the image movement correcting system according to the first embodiment. With reference to FIG. 3, the image movement correcting system 2 according to the first embodiment includes, as its function, an imaging section 310, a display section 320, a visual field moving instruction acquiring section 330, and a control section 340.

The imaging section 310 corresponds to the imaging section 111 shown in FIG. 1. The imaging section 310 acquires video data obtained by photographing an observation target during surgery at any time, and, transmits the acquired video data to a later-mentioned memory section 341 of the control section 340.

The display section 320 includes the display device 20 shown in FIG. 1. The display section 320 displays an image photographed by the imaging section 310 on the basis of the video data having been subjected to image processing appropriately by a later-mentioned image processing section 344 of the control section 340.

In this connection, hereinafter, for distinction, video data acquired by the imaging section 310 are also referred to as imaged video data, and video data to be displayed by the display section 320 (i.e., video data after having applied various kinds of image processing to the imaged video data) is also referred to as display video data.

The visual field moving instruction acquiring section 330 acquires an instruction (hereinafter, also merely referred to as visual field moving instruction) with regard to the movement of the explicit visual field relative to an image displayed on the display section 320. The visual field moving instruction may mean an instruction (namely, instruction indicating that the imaging section 111 is moved) indicating that the microscope section 110 shown in FIG. 1 is moved. Here, an explicit visual field moving instruction means an intentional visual field moving instruction by a surgeon.

As mentioned in the above, since a mode in which, in a free mode, a surgeon moves the microscope section 110 by a direct operation, is supposed in the observation device 10, the visual field moving instruction acquiring section 330 may include, for example, an operation mode changing SW 153 shown in FIG. 1. In the case where an operation indicating that an operation mode of the supporting section 120 is made to a free mode, is input to the operation mode changing SW 153, the visual field moving instruction acquiring section 330 can acquire a visual field moving instruction. The reason is that a period when the operation mode changing SW 153 has been operated and the operation mode has become a free mode, can be deemed as a situation where an instruction about the movement of the microscope section 110 has been input by a direct operation by a surgeon. In the case of having acquired the visual field moving instruction, the visual field moving instruction acquiring section 330 transmits information indicating that the visual field moving instruction has been acquired, to a later-mentioned discriminating section 342 of the control section 340.

In this connection, the first embodiment should not be limited to this example, and the visual field moving instruction may be acquired by other methods. For example, the visual field moving instruction acquiring section 330 may include various kinds of input devices (the above-mentioned remote control terminal, a foot switch, a pressure sensitive sensor, and so on) not illustrated in FIG. 1, and, may acquire a visual field moving instruction in the case where a surgeon has made an operation indicating that the microscope section 110 is moved, to these input devices. Alternatively, in the case where the observation system 1 is equipped with a navigation device that issues an instruction about the movement of the microscope section 110, the visual field moving instruction acquiring section 330 may include a communication device etc. that receive an instruction from the navigation device, and in the case of acquiring an instruction from the navigation device, it may acquire a visual field moving instruction.

The control section 340 includes a control base board etc. on which a processor such as a CPU, and a memory element, such as a memory, are mounted. In this connection, the control section 340 may include the control device 140 shown in FIG. 1, or, may include a device separate from the control device 140. The control section 340 controls various kinds of processes in the image movement correcting system 2 comprehensively. The control section 340 includes, as its function, the memory section 341, the discriminating section 342, and a correcting section 343. In the case where a processor included in the control section 340 operates in accordance with a predetermined program, these functions are realized.

The memory section 341 includes a memory element, such as a memory. The memory section 341 memorizes imaged video data acquired by the imaging section 310. The memory section 341 can temporarily memorize imaged video data in an amount corresponding to a predetermined time necessary for performing a later-mentioned discriminating process with regard to existence or nonexistence of an occurrence of an image movement by the discriminating section 342 and an image movement correcting process by the correcting section 343. The memory section 341 memorizes the imaged video data, in an amount corresponding to the above-mentioned predetermined time, including the newest imaged video data while updating the imaged video data at any time. The memory section 341 provides the memorized imaged video data to the discriminating section 342 and the correcting section 343 appropriately if needed.

The discriminating section 342 discriminates existence or nonexistence of an input of a visual field moving instruction and existence or nonexistence of an occurrence of an image movement. In concrete terms, the discriminating section 342 discriminates existence or nonexistence of an input of a visual field moving instruction on the basis of information indicating having acquired a visual field moving instruction transmitted from the visual field moving instruction acquiring section 330. Moreover, the discriminating section 342 discriminates existence or nonexistence of an occurrence of an image movement by analyzing the imaged video data memorized in the memory section 341. For example, the discriminating section 342 can discriminate the existence of occurrence of an image movement by calculating a difference between the newest imaged video data and the past imaged video data (for example, the imaged video data immediately before that).

The discriminating section 342 provides the information about the discrimination result with regard to the existence or nonexistence of an input of a visual field moving instruction and the existence or nonexistence of an occurrence of an image movement to the correcting section 343.

The correcting section 343 performs the image movement correcting process in the case where the discriminating section 342 has discriminated that there is no input of a visual field moving instruction and that the image movement is occurring. That is because it is thought that the above-described case is a case where an image movement unintended by a surgeon is occurring. For example, even though an operation indicating that the operation mode of the supporting section 120 is set to a free mode is not input to the operation mode changing SW 153, in the case where an image movement is occurring, it is expected that an unintended image shift is occurring. Moreover, for example, even though an operation input indicating that the microscope section 110 is moved has not been performed to various kinds of input devices, or, an instruction indicating that the microscope section 110 is moved has not been input from the navigation device, in the case where the image movement is occurring, it is expected that unintended image shake is occurring.

Figure 4:
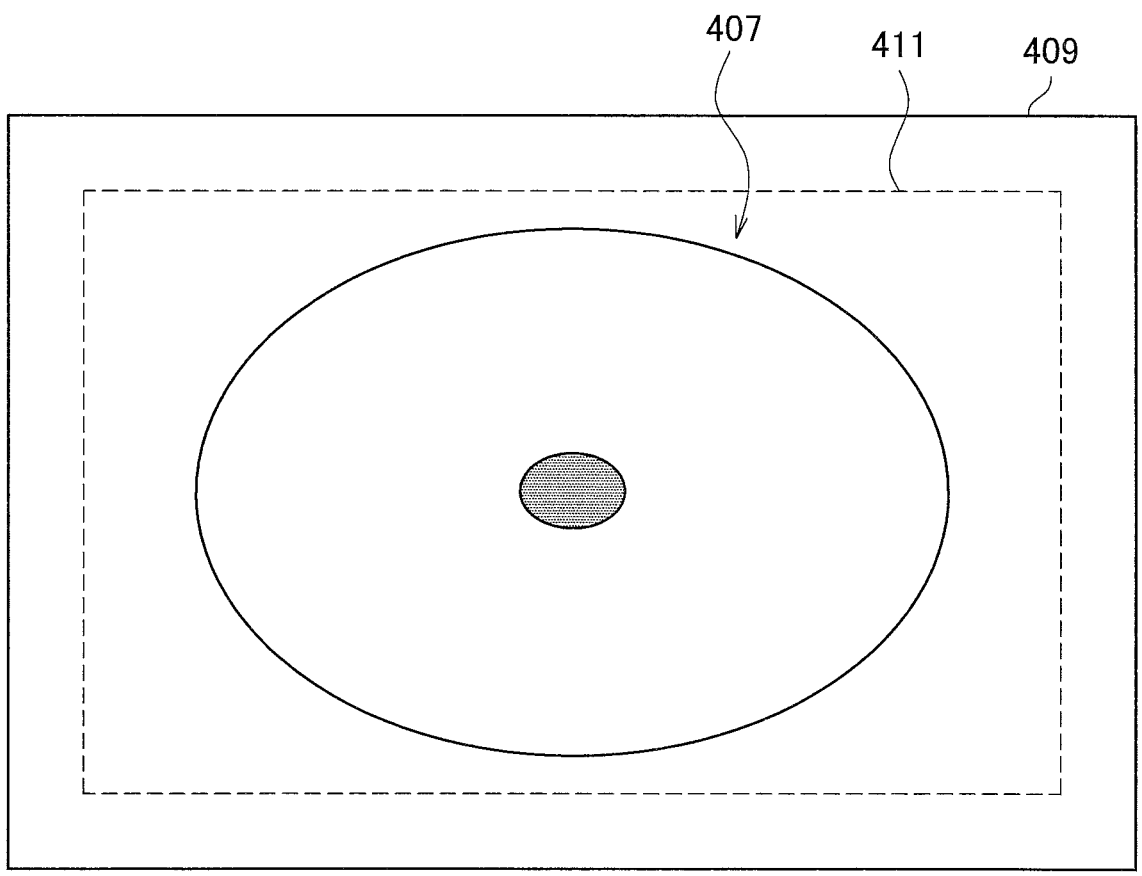
FIG. 4 is an illustration for describing a creating process of display video data in which an image movement has been corrected by an image processing section.

Here, the image correcting process means a process of creating display video data on the basis of imaged video data by correcting an image movement. In concrete terms, in the first embodiment, the correcting section 343 functions as the image processing section 344, and, creates display video data in which an image movement has been corrected by performing image processing appropriately to imaged video data. FIG. 4 is an illustration for describing a creating process of display video data in which an image movement has been corrected by the image processing section 344.

FIG. 4 shows, in a simulative manner, an imaged image 409 of a surgical site 407 photographed by the imaging section 310. As shown in FIG. 4, the image processing section 344 cuts out a predetermined region 411 in the imaged image 409, and, creates display video data by applying various kinds of image processing (for example, gamma correction, adjustment of white balance, enlargement according to an electronic zoom function, inter-pixel correction, etc.) to video data in this cut-out region 411. In the image processing, various kinds of image processing generally performed in order to display an image, may be performed. At this time, the image processing section 344 calculates a movement amount and a movement direction of an image in an image movement by analyzing the imaged video data memorized in the memory section 341, and, adjusts a cut-out position of the region 411 appropriately so as to cancel the image movement correspondingly to the calculated movement amount and movement direction, whereby display video data in which the image movement has been corrected, can be created.

On the other hand, in the case where the discriminating section 342 has discriminated that a visual field moving instruction has been input, or in the case where the discriminating section 342 has discriminated that an image movement has not occurred, it may be considered that an unintended image movement has not occurred. In this case, the correcting section 343, i.e., the image processing section 344, does not perform the correcting process of an image movement, but performs only the usual image processing to the imaged video data, and creates display video data. At this time, also, the image processing section 344 cuts out a predetermined region 411 in an imaged image 409, and, creates display video data. However, the image processing section 344 only cuts out the predetermined region 411 designated beforehand, but does not perform a process of adjusting the position of the region 411 correspondingly to a movement amount and movement direction of an image movement. The predetermined region 411 in the case of not correcting an image movement may be set as a region that has a center at a position same as that of the center of the imaged image 409 and a shape similar to that of the imaged image 409.

That is, in the first embodiment, the image processing section 344 cuts out a predetermined region 411 from the imaged image 409 and creates display video data by performing various kinds of image processing to the imaged video data corresponding to the region 411. However, at this time, in the case where an unintended image movement has not occurred, the image processing section 344 cuts out the predetermined region 411, and in the case where an unintended image movement has occurred, the image processing section 344 adjusts a cut-out position of the region 411 so as to cancel the image movement. With this, even in the case where an unintended image movement has occurred, display video data in which the image movement has been corrected is created.

The image processing section 344 transmits the created display video data to the display section 320, and, makes the display section 320 displays an image on the basis of the display video data. As described in the above, in the case where an unintended image movement has occurred, display video data in which the image movement has been corrected are created. Accordingly, to a surgeon, a more stable image in which an image movement is suppressed is provided. Therefore, it becomes possible to perform surgery more smoothly and more safely.

In the above, a functional constitution of the image movement correcting system 2 according to the first embodiment has been described.

(1-3. Image Movement Correcting Method)

Figure 5:
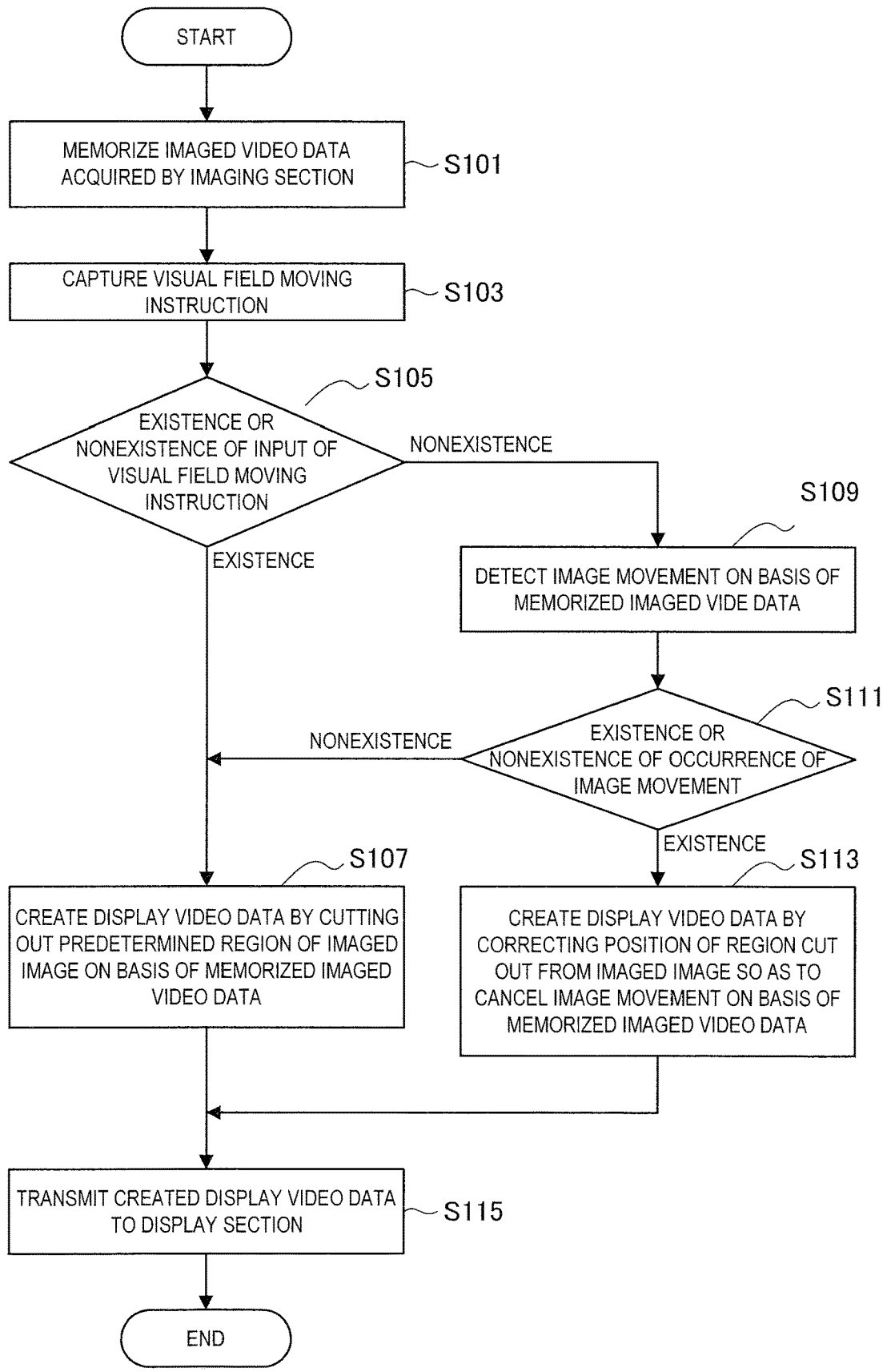
FIG. 5 is a flowchart showing one example of a processing procedure of an image movement correcting method according to the first embodiment.

With reference to FIG. 5, a processing procedure of an image movement correcting method according to the first embodiment is described. FIG. 5 is a flowchart showing one example of the processing procedure of the image movement correcting method according to the first embodiment. In this connection, respective processes shown in FIG. 5 correspond to the processes executed by the control section 340 of the image movement correcting system 2 shown in FIG. 3. The details of these respective processes have already been described at the time of describing a functional constitution of the image movement correcting system 2. Accordingly, in the following description about the processing procedure of the image movement correcting method, the detailed description about the respective processes is omitted.

With reference to FIG. 5, in the image movement correcting method according to the first embodiment, first, imaged video data acquired by the imaging section 310 are memorized (Step S101). The process in Step S101 corresponds to the process executed by the memory section 341 shown in FIG. 3.

Next, capturing of a visual field moving instruction is performed (Step S103). The process in Step S103 corresponds to the process in which the information indicating that a visual field moving instruction acquired by the visual field moving instruction acquiring section 330 shown in FIG. 3 has been input, is transmitted to the control section 340.

Next, the existence or nonexistence of an input of a visual field moving instruction is discriminated (Step S105). The process in Step S105 corresponds to the process executed by the discriminating section 342 shown in FIG. 3.

In the case where it has been discriminated that there exists an input of a visual field moving instruction in Step S105, it proceeds to Step S107. In this case, since it is thought that a surgeon is moving intentionally the microscope section 110, it is not necessary to perform the image movement correcting process. Therefore, without performing the image movement correcting process, in Step S107, on the basis of the memorized imaged video data, a predetermined region (for example, a predetermined region centering on the same position as the center of the imaged image) of the imaged image is cut out, and various kinds of image processing are performed to the imaged video data corresponding to this cut-out region, whereby display video data are created. In this connection, the process in Step S107 corresponds to the process executed by the image processing section 344 shown in FIG. 3.

On the other hand, in Step S105, in the case where it has been discriminated that there does not exist an input of a visual field moving instruction, it proceeds to Step S109. In Step S109, an image movement is detected on the basis of the memorized imaged video data. Then, in Step S111, on the basis of this detection result, the existence or nonexistence of an occurrence of an image movement is discriminated. The processes in Step S109 and Step S111 correspond to the process executed by the discriminating section 342 shown in FIG. 3.

In Step S111, in the case where it has been discriminated that there does not exist occurrence of an image movement, naturally, it is not necessary to perform the image movement correcting process. Therefore, similarly to the case where it has been discriminated that there exists an input of a visual field moving instruction, it proceeds to Step S107, and display video data are created without performing the image movement correcting process.

On the other hand, in Step S111, in the case where it has been discriminated that there exists occurrence of an image movement, it is thought that an image movement unintended by the surgeon is occurring. Therefore, in this case, it proceeds to S113, on the basis of the memorized imaged video data, a position of a region to be cut out from the imaged image is adjusted so as to cancel the image movement, and various kinds of image processing are performed to the imaged video data corresponding to this cut-out region, whereby display video data are created. In this connection, the process in Step S113 corresponds to the process executed by the correcting section 343 shown in FIG. 3, i.e., the image processing section 344.

Upon ending the process in Step S107 or Step S113, the created display video data are transmitted to the display section 320 (Step S115). Then, an image based on the display video data is made to display on the display section 320. In this connection, the process in Step S115 corresponds to the process executed by the image processing section 344 shown in FIG. 3.

In the above, the processing procedure of the image movement correcting method according to the first embodiment has been described.

2. Second Embodiment

The second embodiment of the present disclosure is described. It should be noted that the second embodiment corresponds to one in which a method of a discriminating process of existence or nonexistence of an occurrence of an image movement and a method of an image movement correcting process are different from those in the above-mentioned first embodiment. Since the constitution other than those is similar to that in the first embodiment, in the following description about the second embodiment, the description is made to be mainly given for the matters different from the first embodiment, and the detailed description about the overlapping matters is omitted.

(2-1. Functional Constitution of Image Movement Correcting System)

Figure 6:
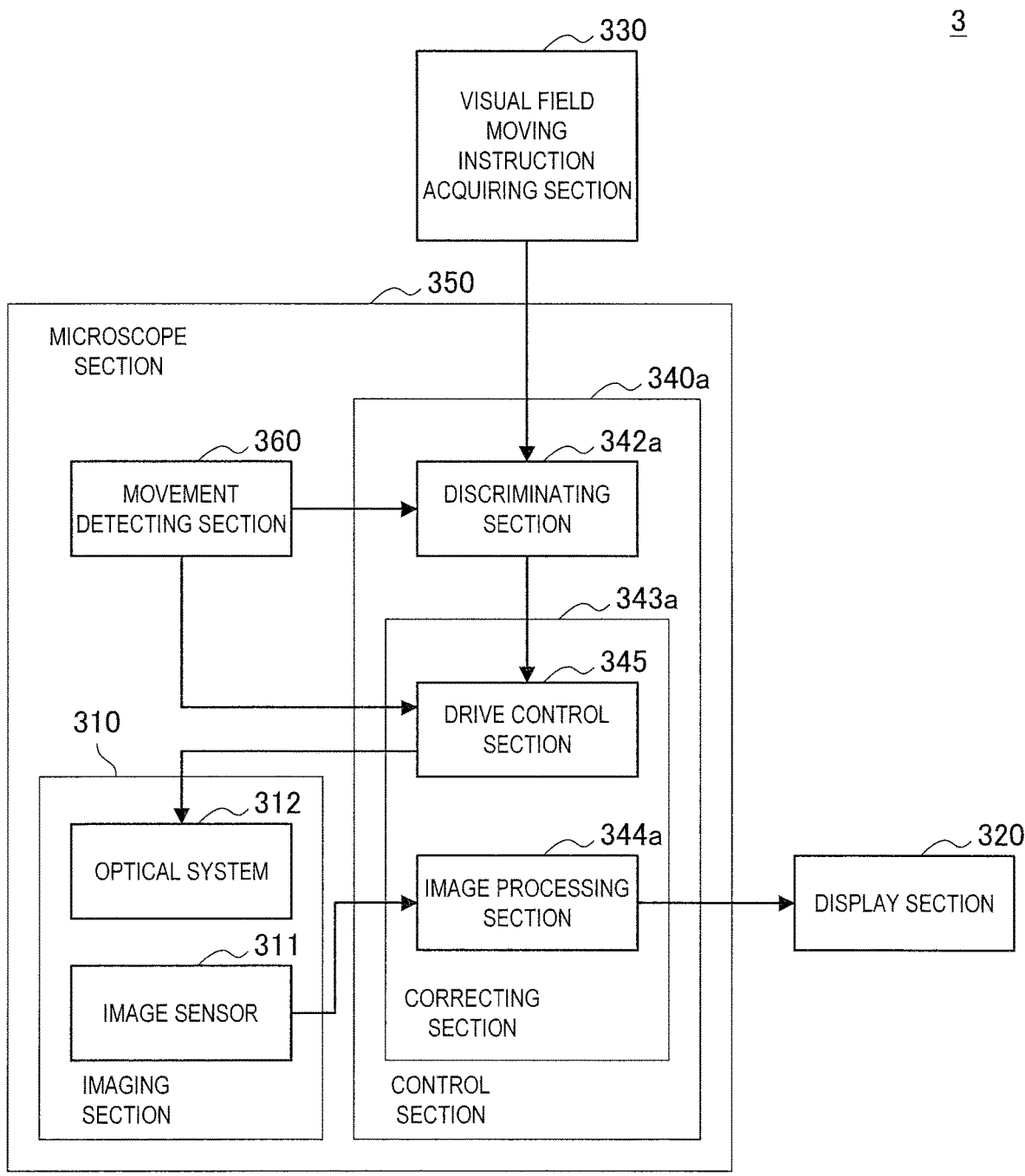
FIG. 6 is a block diagram showing one example of a functional constitution of an image movement correcting system according to the second embodiment.

Since a constitution of an observation system to which an image movement correcting system according to the second embodiment is applied is similar to that of the observation system 1 according to the first embodiment having been described with reference to FIG. 1, the description for it is omitted. Here, with reference to FIG. 6, a constitution of an image movement correcting system according to the second embodiment is described. FIG. 6 is a block diagram showing one example of a functional constitution of the image movement correcting system according to the second embodiment.

With reference to FIG. 6, the image movement correcting system 3 according to the second embodiment includes, as its function, a display section 320, a visual field moving instruction acquiring section 330, and a microscope section 350. Moreover, the microscope section 350 includes, as its function, an imaging section 310, a control section 340a, and a movement detection section 360.

Among these, the functions of the imaging section 310, the display section 320, and the visual field moving instruction acquiring section 330 are almost similar to those in the first embodiment. That is, the imaging section 310 acquires video data obtained by photographing an observation target during surgery at any time, and, provides to a later-mentioned image processing section 344a of the control section 340a. In this connection, in FIG. 6, for description, blocks showing an image sensor 311 and an optical system 312 (lens etc.) that constitute the imaging section 310 are also illustrated. The display section 320 displays an image photographed by the imaging section 310 on the basis of display video data created by the later-mentioned image processing section 344a of the control section 340a. The visual field moving instruction acquiring section 330 acquires a visual field moving instruction, and, provides to the later-mentioned discriminating section 342a of the control section 340a.

The microscope section 350 corresponds to the microscope section 110 shown in FIG. 1. Moreover, the control section 340a includes a control base board etc. on which a processor, such as a CPU, or, a memory element, such as a program and a memory, are mounted. Moreover, the movement detecting section 360 includes a sensor capable of detecting a movement (more specifically, movement of the imaging section 310) of the microscope sections 350, such as an acceleration sensor, a gyro sensor, or the like. In this way, in the second embodiment, as a hardware constitution, the microscope section 350 may include the imaging section 310, a processor, a control base board, or the like corresponding to the control section 340a, and a sensor corresponding to the movement detecting section 360. Hereinafter, the functions of the control section 340a and the movement detecting section 360 are described in more details.

The movement detecting section 360 detects a movement of the imaging section 310, and, acquires the movement information showing the movement of the imaging section 310. The kind of the sensor constituting the movement detecting section 360 should not be limited, and, various kinds of sensors generally used at the time of detecting a movement of an object, such as the above-mentioned acceleration sensor or gyro sensor, may be used. However, as mentioned later, in the second embodiment, the discriminating process of existence or nonexistence of an occurrence of an image movement and an image movement correcting process are performed on the basis of the movement information acquired by the movement detecting section 360. Therefore, it is preferable that the movement detecting section 360 is constituted to be able to detect at least a movement of the imaging section 310 in an in-plane direction parallel to the light receiving surface of the image sensor 311 of the imaging section 310. Moreover, in terms of hardware, it is preferable that the sensor constituting the movement detecting section 360 is installed comparatively in the vicinity of the imaging section 310 so as to be able to detect the vibration of the imaging section 310 with high accuracy. Furthermore, it is preferable that in order to make the microscope section 350 small in size, the sensor constituting the movement detecting section 360 is also comparatively small in size.

The movement detecting section 360 provides the acquired movement information to the later-mentioned discriminating section 342a and correcting section 343a of the control section 340a.

The control section 340a controls various kinds of processing in the image movement correcting system 3 comprehensively. The control section 340a includes, as its function, the discriminating section 342a and the correcting section 343a. In the case where a processor constitution the control section 340a operates in accordance with a predetermined program, these functions are realized. In this connection, as mentioned above, although the control section 340a may include a processor or a control base board etc., these may be the same device as the control device 140 shown in FIG. 1, or a part of the control devices 140, or may be a separate device from the control device 140.

The discriminating section 342a discriminates existence or nonexistence of an input of a visual field moving instruction and existence or nonexistence of an occurrence of an image movement. In concrete terms, the discriminating section 342a discriminates the existence or nonexistence of an input of a visual field moving instruction on the basis of information indicating having acquired a visual field moving instruction, provided from the visual field moving instruction acquiring section 330. This discriminating process of the existence or nonexistence of an input of a visual field moving instruction is similar to that in the first embodiment.

In the second embodiment, a method of the discriminating process of existence or nonexistence of an occurrence of an image movement is different from that in the first embodiment. In concrete terms, the discriminating section 342a discriminates existence or nonexistence of an occurrence of an image movement on the basis of the movement information provided from the movement detecting section 360. For example, in the case where a movement of the imaging section 310 in an in-plane direction parallel to the light receiving surface of the image sensor 311 is detected by the movement detecting section 360, the discriminating section 342a discriminates that an image movement has occurred.

The discriminating section 342a provides the information about the discrimination result with regard to the existence or nonexistence of an input of a visual field moving instruction and the existence or nonexistence of an occurrence of an image movement to the correcting section 343a.

The correcting section 343a performs the image movement correcting process in the case where the discriminating section 342a has discriminated that there does not exist input of a visual field moving instruction and that the image movement is occurring. Similarly to the first embodiment, it is because it is thought that the above-described case is a case where an image movement unintended by a surgeon is occurring.

Also in the second embodiment, similarly to the first embodiment, in the image correcting process, an image movement is corrected, and display video data are created on the basis of imaged video data. However, in the second embodiment, its concrete processing method, i.e., the function of the correcting section 343a is different from that in the first embodiment. In concrete terms, in the second embodiment, the correcting section 343a functions as the drive control section 345 that makes the optical system 312 of the imaging section 310 drive and the image processing section 344a that creates display video data by applying image processing appropriately to imaged video data.

On the basis of the movement information provided from the movement detecting section 360, the drive control section 345 calculates a movement amount and movement direction of an image in an image movement, and, calculates a movement amount of a lens included in an optical system 312 that guides observation light to the image sensor 311, so as to cancel the image movement correspondingly to the calculated movement amount and movement direction. Then, by moving the lens appropriately in accordance with the calculated movement amount, the drive control section 345 corrects an image movement. In this connection, to a lens moving process to cancel an image movement by this drive control section 345, a technique according to a so-called hand shake preventing function of a lens shift system mounted on digital cameras etc. may be applied.

The image processing section 344a creates display video data by applying various kinds of image processing (for example, gamma correction, adjustment of white balance, enlarging according to an electronic zoom function, inter-pixel correction, etc.) to imaged video data acquired by the imaging section 310. In the image processing, various kinds of image processing generally performed in order to display an image may be performed. As mentioned in the above, since the lens of the optical system 312 of the imaging section 310 is appropriately moved by the drive control section 345, the imaged video data that the image processing section 344a acquires, have become one in which an image movement has been corrected. That is, the image processing section 344a can create display video data in which an image movement has been corrected.

The image processing section 344a transmits the created display video data to the display section 320, and, makes the display section 320 display an image on the basis of the display video data. As described in the above, in the case where an unintended image movement has occurred, display video data in which the image movement has been corrected are created. Accordingly, to a surgeon, a more stable image in which an image movement is suppressed is provided. Therefore, it becomes possible to perform surgery more smoothly and more safely.

In the above, the functional constitution of the image movement correcting system 3 according to the second embodiment has been described. In this connection, in the above-mentioned constitution example, although the correcting section 343a has corrected an image movement using the technique according to the so-called lens shift system, the second embodiment should not be limited to this example. In the second embodiment, the correcting section 343a may correct an image movement using other methods. For example, the correcting section 343a can correct an image movement using various kinds of techniques according to a so-called optical type correcting method used in a hand shake preventing function mounted on digital cameras and so on. Here, the optical type correcting method is a method of adjusting a light receiving position of observation light in the image sensor 311 and correcting an image movement by moving a position of the image sensor 311 of the imaging section 310 or the optical systems 312 (for example, lens etc.) on the basis of a detected movement of the imaging section 310. The above-mentioned lens shift system is also one of the optical type correcting methods. As the optical type correcting method, in addition to the above-mentioned lens shift system, an image sensor shift system, a lens unit swing system, etc. are known. The correcting section 343a may correct an image movement in accordance with various kinds of these systems.

(2-2. Image Movement Correcting Method)

Figure 7:
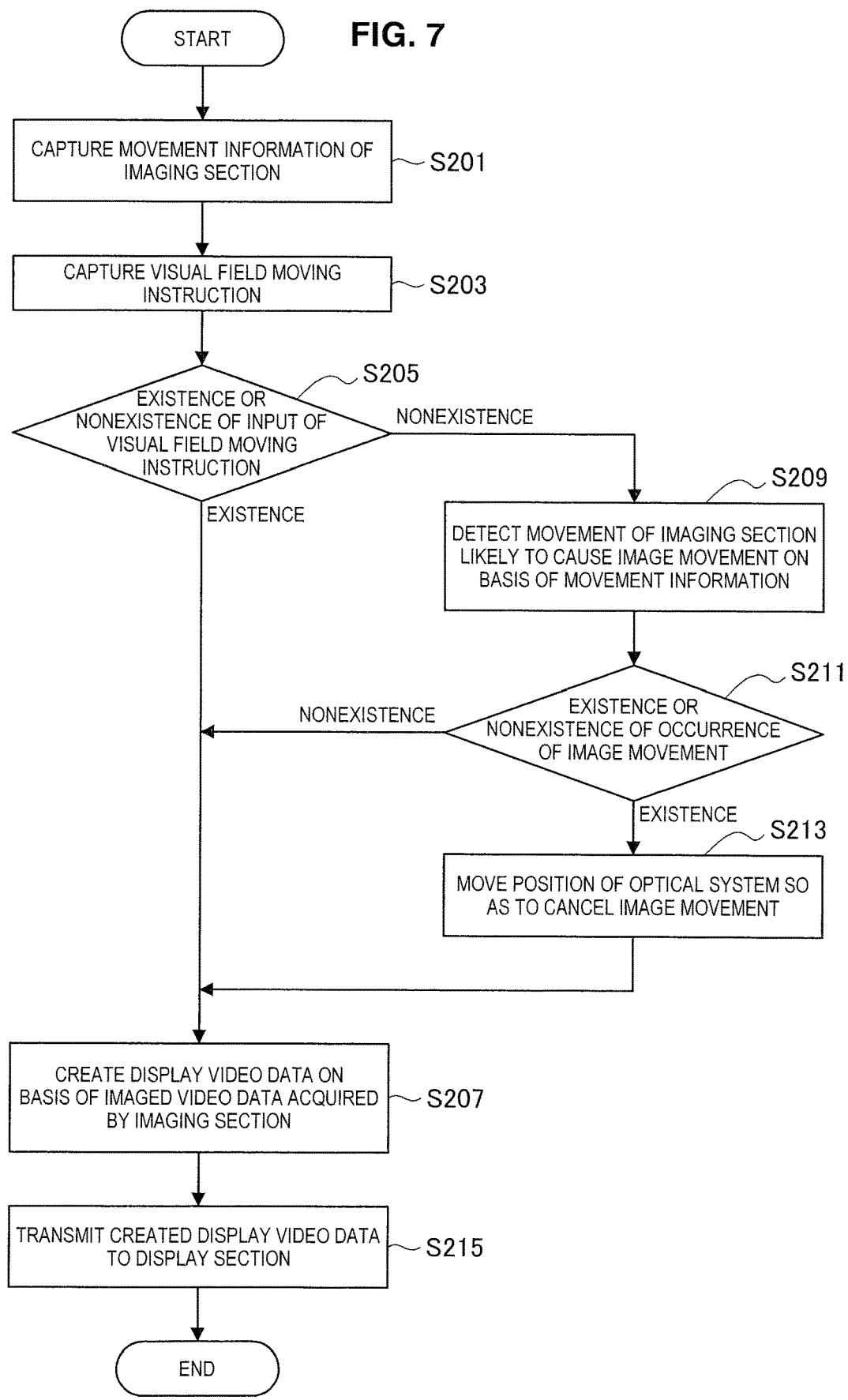
FIG. 7 is a flowchart showing one example of a processing procedure of an image movement correcting method according to the second embodiment.

With reference to FIG. 7, the processing procedure of an image movement correcting method according to the second embodiment is described. FIG. 7 is a flowchart showing one example of the processing procedure of the image movement correcting method according to the second embodiment. In this connection, respective processes shown in FIG. 7 correspond to the processes executed by the control section 340a of the image movement correcting system 3 shown in FIG. 6. The details of these respective processes have already been described at the time of describing the functional constitution of the image movement correcting system 3. Accordingly, in the following description about the processing procedure of the image movement correcting method, the detailed description about the respective processes is omitted.

With reference to FIG. 7, in the image movement correcting method according to the second embodiment, first, capturing of the movement information of the imaging section 310 is performed (Step S201). The process in Step S201 corresponds to the process in which the movement information of the imaging section 310 acquired by the movement detecting section 360 shown in FIG. 6 is provided to the control section 340a.

Next, capturing of a visual field moving instruction is performed (Step S203). The process in Step S203 corresponds to the process in which the information indicating that the visual field moving instruction acquired by the visual field moving instruction acquiring section 330 shown in FIG. 6 has been input is transmitted to the control section 340a.

Next, the existence or nonexistence of an input of a visual field moving instruction is discriminated (Step S205). The process in Step S205 corresponds to the process executed by the discriminating section 342a shown in FIG. 6.

In Step S205, in the case where it has been discriminated that there exists an input of a visual field moving instruction, it proceeds to Step S207. In this case, since it is thought that a surgeon is moving intentionally the microscope section 110, it is not necessary to perform the image movement correcting process. Therefore, without performing an image movement correcting process, in Step S207, various kinds of image processing are performed to the imaged video data acquired by the imaging section 310, whereby display video data are created. In this connection, the process in Step S207 corresponds to the process executed by the image processing section 344a shown in FIG. 6.

On the other hand, in Step S205, in the case where it has been discriminated that there does not exist an input of a visual field moving instruction, it proceeds to Step S209. In Step S209, a movement (in concrete terms, for example, a movement of the imaging section 310 in an in-plane direction parallel to a light receiving surface of the image sensor 311) of the imaging section 310 that is likely to cause an image movement, is detected on the basis of the movement information acquired in Step S201. Then, in Step S211, on the basis of this detection result, the existence or nonexistence of an occurrence of an image movement is discriminated. The processes in Step S209 and Step S211 correspond to the processes executed by the discriminating section 342a shown in FIG. 6.

In Step S211, in the case where it has been discriminated that there does not exist occurrence of an image movement, naturally, it is not necessary to perform the image movement correcting process. Therefore, similarly to the case where it has been discriminated that there exists an input of a visual field moving instruction, it proceeds to Step S207, and display video data are created without performing the image movement correcting process.

On the other hand, in Step S211, in the case where it has been discriminated that there exists occurrence of an image movement, it is thought that an image movement unintended by a surgeon is occurring. Therefore, in this case, it proceeds to S213, the position of the optical system 312 of the imaging section 310 is moved so as to cancel an image movement. In this connection, the process in Step S213 corresponds to the process executed by the drive control section 345 of the correcting section 343a shown in FIG. 6.

Upon ending the process in Step S213, it proceeds to Step S207, various kinds of image processing are applied to the imaged video data acquired by the imaging section 310, whereby display video data are created. By performing the process in Step S213, the imaged video data acquired by the imaging section 310 has become one in which the image movement has been corrected. Accordingly, in Step S207, the display video data in which the image movement has been corrected are created.

Upon ending the process in Step S207, the created display video data are transmitted to the display section 320 (Step S215). Then, an image on the basis of the display video data is made to be displayed on the display section 320. In this connection, the process in Step S215 corresponds to the process executed by the image processing section 344a shown in FIG. 6.

In the above, the processing procedure of the image movement correcting method according to the second embodiment has been described.

3. Supplement

The preferred embodiments of the present disclosure have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, the respective constitutions in each of the above-described embodiments may be combined with each other within a possible range. For example, in the observation device 10, the discriminating process of the existence or nonexistence of an occurrence of an image movement according to the first embodiment (i.e., the method of discriminating by comparing the newest imaged video data with the past imaged video data) and the discriminating process of the existence or nonexistence of an occurrence of an image movement according to the second embodiment (i.e., the method of discriminating on the basis of the movement information of the imaging section 310) may be performed together. In this case, for example, in the case where it has been discriminated that the image movement is occurring in any of them, it may be discriminated finally that the image movement is occurring. The existence or nonexistence of an occurrence of an image movement is discriminated separately by two methods different from each other, whereby it becomes possible to perform the discriminating process more accurately.

Moreover, in the above, as one example, although a case of performing surgery using the observation system 1 has been described, the present technology should not be limited to this example. As described in the above, according to the first and second embodiments, it becomes possible to obtain a more stable image in which an unintended image movement has been suppressed. Therefore, for example, in various kinds of medical practices that may be performed using the observation system 1, such as an inspection, it is possible to attain the similar effects.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A medical observation device, including:
an imaging section that acquires imaged video data being video data obtained by photographing an observation target;
a supporting section that supports the imaging section;
a discriminating section that discriminates existence or nonexistence of an input of a visual field moving instruction to an image to be displayed on a display device on a basis of the imaged video data and existence or nonexistence of an occurrence of an image movement to an image to be displayed on the display device on a basis of the imaged video data; and
a correcting section that creates display video data being video data to be displayed on the display device on a basis of the imaged video data by correcting the image movement in a case where the discriminating section has discriminated that there does not exist an input of the visual field moving instruction and the image movement is occurring.

(2)

The medical observation device according to (1), in which the discriminating section discriminates existence or nonexistence of an input of the visual field moving instruction correspondingly to existence or nonexistence of an operation input indicating that the imaging section is moved via an input device.

(3)

The medical observation device according to (1) or (2), in which the discriminating section discriminates existence or nonexistence of an input of the visual field moving instruction correspondingly to existence or nonexistence of an input of an instruction from a navigation apparatus that issues the instruction indicating that the imaging section is moved to the medical observation device.

(4)

The medical observation device according to any one of (1) to (3), in which the discriminating section discriminates existence or nonexistence of an occurrence of the image movement by comparing the newest imaged video data with the imaged video data acquired in past.

(5)

The medical observation device according to any one of (1) to (4), further including:

a movement detecting section that acquires movement information indicating movement of the imaging section, in which the discriminating section discriminates existence or nonexistence of an occurrence of the image movement on a basis of the movement information.

(6)

The medical observation device according to any one of (1) to (5), in which when creating the display video data by cutting out a predetermined region of an image relating to the imaged video data, the correcting section corrects the image movement by adjusting a cutting-out position of the predetermined region.

(7)

The medical observation device according to any one of (1) to (5), further including:

a movement detecting section that acquires movement information indicating movement of the imaging section, in which the correcting section corrects the image movement by moving a position of an image sensor or an optical system that constitutes the imaging section, on a basis of the movement information.

(8)

The medical observation device according to any one of (1) to (7), in which display video data created by the correcting section are displayed on the display device by being enlarged by two times or more with an electronic zoom function.

(9)

The medical observation device according to any one of (1) to (8), in which in the supporting section, a diameter of a thinnest portion is 30 mm or less.

(10)

An image movement correcting method, including:

capturing imaged video data being video data obtained by photographing an observation target;

discriminating, by a processor, existence or nonexistence of an input of a visual field moving instruction to an image to be displayed on a display device on a basis of the imaged video data and existence or nonexistence of an occurrence of an image movement to an image to be displayed on the display device on a basis of the imaged video data; and a correcting section that creates display video data being video data to be displayed on the display device on a basis of the imaged video data by correcting the image movement in a case where it has been discriminated that there does not exist an input of the visual field moving instruction and the image movement is occurring.

(11)

A medical observation system, including:

a medical observation device that photographs an observation target; and a display device that displays an image of the observation target photographed by the medical observation device, in which the medical observation device includes an imaging section that acquires imaged video data being video data obtained by photographing an observation target, a supporting section that supports the imaging section, a discriminating section that discriminates existence or nonexistence of an input of a visual field moving instruction to an image to be displayed on the display device on a basis of the imaged video data and existence or nonexistence of an occurrence of an image movement to an image to be displayed on the display device on a basis of the imaged video data, and a correcting section that creates display video data being video data to be displayed on the display device on a basis of the imaged video data by correcting the image movement in a case where the discriminating section has discriminated that there does not exist an input of the visual field moving instruction and the image movement is occurring.

REFERENCE SIGNS LIST 1 observation system
2, 3 image movement correcting system
10 microscope device
20 display device
110 microscope section
111, 310 imaging section
112 barrel section
120 supporting section (arm section)
130 base section
131 platform
132 casters
140 control device
151 zoom SW
152 focus SW
153 operation mode changing SW
210 first rotational axis section
220 second rotational axis section
230 third rotational axis section
240 fourth rotational axis section
250 fifth rotational axis section
260 sixth rotational axis section
241, 242, 243, 244 arm
245, 246, 247, 248 joint section
271 first arm section
272 second arm section
273 third arm section
274 fourth arm section
320 display section
330 visual field moving instruction acquiring section
340, 340a control section
341 memory section
342, 342a discriminating section
343, 343a correcting section
344, 344a image processing section
345 drive control section

The invention claimed is:

1. A controller for a medical observation device, comprising:
a circuitry configured to:
receive a video image of an observation target from a camera;
determine existence or nonexistence of a visual field moving instruction and existence or nonexistence of image movement in the video image;
output display data to be displayed on a display by correcting the image movement in the video image on condition that the visual field moving instruction does not exist and image movement is occurring, otherwise output the video image as display data to be displayed on the display; and on condition that the visual field moving instruction does not exist and image movement is occurring, the circuitry is configured to correct image movement based on a position in accordance with stored image data or by moving a position of an image sensor or an optical system that constitutes the camera.

2. The controller according to claim 1, wherein the circuitry is configured to determine existence or nonexistence of the visual field moving instruction correspondingly to existence or nonexistence of an operation input indicating that the camera is moved.

3. The controller according to claim 1, wherein the circuitry is configured to discriminate existence or nonexistence of the visual field moving instruction correspondingly to existence or nonexistence of an instruction from a navigation apparatus that issues the instruction indicating that the camera is moved.

4. The controller according to claim 1, wherein the circuitry is configured to discriminate existence or nonexistence of the image movement by comparing newest video image with previous video image.

5. The controller according to claim 1, wherein the circuitry is configured to:
detect movement information indicating movement of the camera, and
discriminate existence or nonexistence of the image movement on a basis of the movement information.

6. The controller according to claim 1, wherein the circuitry is configured to cut out a predetermined region of an image relating to the video image, and to correct the image movement by adjusting a position of the predetermined region on condition that the visual field moving instruction does not exist and image movement is occurring.

7. The controller according to claim 1, wherein the circuitry is configured to:
detect movement information indicating movement of the camera,
correct the image movement by moving a position of an image sensor or an optical system that constitutes the camera, on a basis of the movement information.

8. An image movement correcting method, comprising:
receiving a video image obtained by photographing an observation target;
discriminating existence or nonexistence of a visual field moving instruction and existence or nonexistence of image movement in the video image;
outputting display data to be displayed on a display by correcting the image movement on condition that the visual field moving instruction does not exist and image movement is occurring, otherwise outputting the video image as display data to be displayed on the display; and
on condition that the visual field moving instruction does not exist and image movement is occurring, correcting image movement based on a position in accordance with stored image data or by moving a position of an image sensor or an optical system that constitutes the camera.

9. A medical observation system, comprising:
a medical observation device; and
a display that displays an image of output from the medical observation device,
wherein the medical observation device includes
a camera that outputs a video image obtained by photographing an observation target;
a support that supports the camera; and
a circuitry configured to:
determine existence or nonexistence of a visual field moving instruction and existence or nonexistence image movement in the video image;
output display data to be displayed on the display by correcting the image movement in the video image on condition that the visual field moving instruction does not exist and image movement is occurring, otherwise output the video image as display data to be displayed on the display; and
on condition that the visual field moving instruction does not exist and image movement is occurring, the circuitry is configured to correct image movement based on a position in accordance with stored image data or by moving a position of an image sensor or an optical system that constitutes the camera.

10. The medical observation system according to claim 9, wherein display data are displayed on the display by being enlarged with an electronic zoom function.

11. The medical observation system according to claim 9, wherein in the support, a diameter of a thinnest portion is between 10 mm and 30 mm.

12. The medical observation system according to claim 9, wherein the circuitry is configured to determine existence or nonexistence of the visual field moving instruction correspondingly to existence or nonexistence of an operation input indicating that the camera is moved.

13. The medical observation system according to claim 9, wherein the circuitry is configured to discriminate existence or nonexistence of the visual field moving instruction correspondingly to existence or nonexistence of an instruction from a navigation apparatus that issues the instruction indicating that the camera is moved.

14. The medical observation system according to claim 9, wherein the circuitry is configured to discriminate existence or nonexistence of the image movement by comparing newest video image with previous video image.

15. The medical observation system according to claim 9, wherein the circuitry is configured to:
detect movement information indicating movement of the camera, and
discriminate existence or nonexistence of the image movement on a basis of the movement information.

16. The medical observation system according to claim 9, wherein the circuitry is configured to cut out a predetermined region of an image relating to the video image, and to correct the image movement by adjusting a position of the predetermined region on condition that the visual field moving instruction does not exist and image movement is occurring.

17. The medical observation system according to claim 9, wherein the circuitry is configured to:
detect movement information indicating movement of the camera,
correct the image movement by moving a position of an image sensor or an optical system that constitutes the camera, on a basis of the movement information.

* * * * *